(12) United States Patent
Levy et al.

(10) Patent No.: US 7,156,881 B2
(45) Date of Patent: Jan. 2, 2007

(54) COUNTERACTING BIOPROSTHETIC CALCIFICATION

(75) Inventors: Robert J. Levy, Marion Station, PA (US); Ivan Alferiev, Clementon, NJ (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 508 days.

(21) Appl. No.: 10/336,857

(22) Filed: Jan. 6, 2003

(65) Prior Publication Data

US 2003/0196274 A1   Oct. 23, 2003

Related U.S. Application Data

(60) Provisional application No. 60/344,810, filed on Jan. 7, 2002.

(51) Int. Cl.
A61F 2/02 (2006.01)
(52) U.S. Cl. ............................. 8/94.11; 623/1; 623/2; 623/3; 623/4; 623/7; 623/9; 623/10; 623/11; 623/12; 623/13; 623/14; 514/21
(58) Field of Classification Search ................ 8/94.11; 514/21; 623/1–14
See application file for complete search history.

(56) References Cited

U.S. PATENT DOCUMENTS 5,338,731 A   8/1994   Breuer et al.

5,674,298 A   10/1997   Levy et al.

FOREIGN PATENT DOCUMENTS

WO   WO 01/58503 A1   8/2001

OTHER PUBLICATIONS

Alferiev et al., J. Polymer Sci., Part A (Polymer Chemistry) 39:105 (2001).

*Primary Examiner*—Y Gupta
*Assistant Examiner*—Preeti Kumar
(74) *Attorney, Agent, or Firm*—Caesar, Rivise, Bernstein, Cohen & Pokotilow, Ltd.

(57) ABSTRACT

Adapting crosslinking with triglycidyl amine (TGA) to incorporate the use of a particular type of anti-calcification agent provides a broad-reaching solution to the problem in vivo bioprosthesis calcification. The anti-calcification agent in question includes a polyphosphonate compound that contains a functional group, which serves as a reaction site between the polyphosphonate and a polyepoxide. The functional group is reactive enough to dominate the reaction between the polyphosphonate and the polyepoxide, thereby excluding the chelating oxygen atoms of polyphosphonate from the reaction, protecting their anti-calcification ability. Furthermore, the high reactivity of the functional group allows the polyphosphonate to attach to the polyepoxide more completely, which improves the calcification resistance of bioprosthetic material with which the polyepoxide is crosslinked.

17 Claims, 1 Drawing Sheet

Graphical Representation of the Effect of MABP on TGA Cross-linking of Bovine Pericardium

Figure 1. Graphical Representation of the Effect of MABP on TGA Cross-linking of Bovine Pericardium
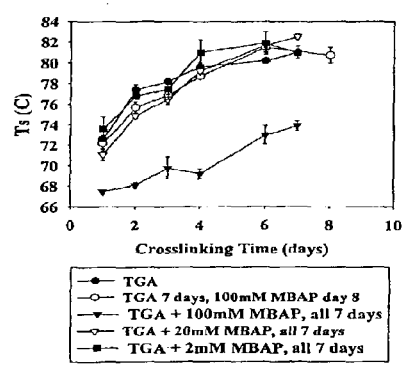
Figure 2. The Graphical Representation of the TGA-MABP Inhibition of Calcification in 21 Day Rat Subdermal Implants Compared to TGA Alone
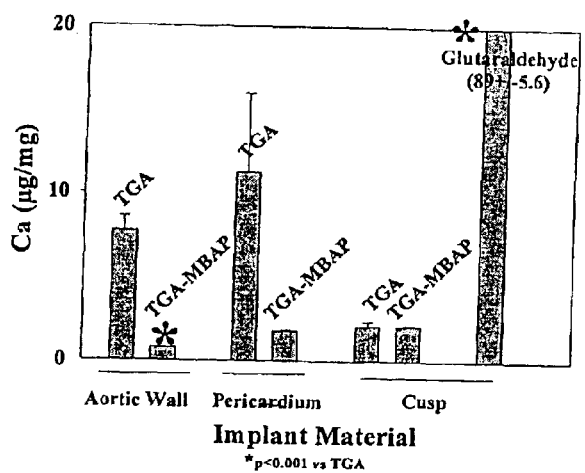

COUNTERACTING BIOPROSTHETIC CALCIFICATION

BACKGROUND

1. Field of Invention

The present invention relates to a strategy for combating the tendency of bioprosthetic material to calcify in vivo.

2. Description of Related Art

Pathologic calcification has limited the use of prostheses that incorporate tissue components. In relation to such "bioprotheses," U.S. Pat. No. 5,674,298 to Levy et al. discusses the problem and one approach to its solution, which entails pretreating a bioprosthetic tissue with a polyphosphonate:polyepoxide monoadduct. The polyepoxide serves to stabilize the bioprosthetic tissue against subsequent in vivo enzymatic degradation by crosslinking with collagen chains of the tissue. While effective for stabilization, the polyepoxide promotes calcification but the polyphosphonate provides chelating oxygen atoms that can counteract the calcification.

The solution advanced in the Levy patent has drawbacks, however. After the pretreatment, the anti-calcification effect on the bioprosthetic material gradually wanes, possibly because the effective agent, the polyphosphonate, is washed out over time. To the extent that polyphosphonates bind tissues covalently, a possibility raised by Levy et al., the anti-calcification efficiency of the polyphosphonates may be impaired because the binding is achieved by partial alkylation of their chelating oxygen atoms, which would disable the function of the chelating oxygen atoms to block the growth of calcium crystals. Applying more polyphosphonates to compensate could affect adversely the crosslinking between the polyepoxide and the prosthetic tissue.

Published international application PCT/US01/58503 discloses another approach that entails the use of crosslinking triglycidyl amine (TGA) to achieve improved calcification resistance for bioprosthetic materials. For instance, TGA treatment has been employed to inhibit in vivo calcification of the valve cusp component in a porcine aortic valve bioprosthesis.

The TGA-crosslinking methodology falls short, however, in the inhibition of calcification in certain parts of a bioprosthetic heart valve. In particular, it is relatively ineffective against calcification of the aortic wall segment of a bioprosthetic implant. It also is less effective at inhibiting bovine pericardial calcification.

SUMMARY OF THE INVENTION

In response to the need for an improved anti-calcification strategy, the present invention yields bioprosthetic material that is characterized by an enhanced, prolonged resistance to pathologic calcification in vivo.

The invention also provides an anti-calcification agent that can bind to a TGA-crosslinking agent without a loss of overall anti-calcification function.

Furthermore, the present invention contemplates using an anti-calcification agent with TGA-crosslinking, in the context of fabricating or treating bioprosthetic materials, without a substantial decline in anti-calcification activity.

To these ends, the present invention provides a method of treating bioprosthetic material, comprising bringing bioprosthetic tissue into contact with a polyepoxide in the presence of an amino-thiol-containing polyphosphonate, at a temperature and for a period such that said bioprosthetic tissue cross-links with said polyepoxide, and said polyphosphonate covalently binds to the polyepoxide through its thiol group, whereby the bioprosthetic tissue displays anti-calcification properties in vivo.

In further accordance with these and other ends, there is provided a bioprosthetic article that has a polyepoxy crosslinking and a thiol-containing polyphosphonate anti-calcification agent covalently bound through the thiol group thereon according to this method.

In another aspect of this invention, these and other ends are achieved by providing a process of preparing an amino-thiol-containing polyphosphonate, comprising (i) reacting an amino-containing disulfide with a vinylic polyphosphonate to form an amino-disulfide-containing polyphosphonate, and (ii) cleaving the disulfide bond to form an amino-thiol-containing polyphosphonate.

BRIEF DESCRIPTION OF THE DRAWINGS

FIG. 1 is a graphical representation of the effect of MABP on TGA cross-linking of bovine pericardium.

FIG. 2 is a graphical representation of the TGA-MABP inhibition of calcification in 21-day rat subdermal implants, compared to TGA alone.

DETAILED DESCRIPTION OF THE INVENTION

The inventors have discovered that incorporating a particular type of anti-calcification agent into the above-discussed TGA-crosslinking methodology offers a more universal solution to the problem in vivo bioprosthesis calcification. The anti-calcification agent of the invention includes a polyphosphonate compound that contains a functional group, which serves as a reaction site between the polyphosphonate and a polyepoxide. According to the invention, the functional group is reactive enough to dominate the reaction between the polyphosphonate and the polyepoxide, thereby excluding the chelating oxygen atoms of polyphosphonate from the reaction, which protects their anti-calcification ability. Furthermore, the high reactivity of the functional group allows the polyphosphonate to attach to the polyepoxide more completely, which improves the calcification resistance of bioprosthetic material with which the polyepoxide is crosslinked.

Preferably, the co-attachment reaction and the cross-linking reaction take place together. Accordingly, the reactivity of the reacting functional group is preferably examined under conditions of pH and temperature that are close to those of the cross-linking reaction.

Pursuant to the present invention, the functional groups need to cleave an epoxy ring, and nucleophilic groups are illustrative in this respect. The inventors have investigated various nucleophiles, and their results, summarized in Table 1 below, point to the type of nucleophiles that are effective for this purpose.

First, it is apparent that, under conditions approximating those of a common epoxy cross-linking reaction (that is, 20° C. and pH of about 7), all nucleophiles that demonstrate reactivity contain a sulfur atom. Thus, nucleophiles that contain a sulfur atom, such as thiosulfate, cysteine, and N-acetyl-DL-methionine, are at least twenty times more reactive than nucleophiles without a sulfur atom.

TABLE I

Kinetics of Epoxy-ring Opening with Different Nucleophiles
(t-butyl glycidyl ether in water, 20° C., pH ca. 7)

| Substrate, concentration | Concentration of epoxide | Time of reaction | Reacted substrate | $k \cdot 10^3$ (l/mol · h) |
|---|---|---|---|---|
| Thiosulfate, 0.1 M | 0.3 M | 5 min | 30% | 23 000 |
|  |  | 15 min | 52% | 17 000 |
| Cysteine,[a] 0.2 M | 0.1 M | 1 h | 13% | 1618 |
| N-Acetyl-DL-methionine,[b] 0.1 M | 0.3 M | 3 h | 33% | 473 |
|  |  | 19 h | 89% | 488 |
| Imidazole,[c] 0.1 M | 0.3 M | 48 h | 28% | 24 |
| N-Acetyl-L-histidine, 0.1 M | 0.3 M | 120 h | 60% | 29 |
| Alk-CH$_2$NH$_2$, 0.1 M | 0.3 M | 45 h | 16% | 13 |
| Alk-CH$_2$COOH, 0.1 M | 0.3 M | 45 h | 6% | 4.6 |
| Phosphate, 0.4 M | 0.3 M | 120 h | 12% | 3.9 |
| HEDP, 0.4 M | 0.3 M | 120 h | 5.5% | 1.6 |

Notes:
[a] Only the thiol group reacts.
[b] Only the methylthio-group reacts.
[c] Model of histidine residue, can react with two molecules of epoxide.

Secondly, both cysteine and N-acetyl-DL-methionine, which are the second and third highest reactive nucleophiles in Table I, also contain a carboxyl group and/or an amino group, which presumably creates favorable conditions for the thiol group to cleave the epoxy ring. While not wishing to be bound by any mechanism, the carboxyl group may protonate an epoxide, stabilizing a transitional open-ring structure, to enhance an acid-catalyzed cleavage reaction. It also is possible that a carboxylate group or an amino group, by forming a hydrogen bond with the proton of the thiol group, creates a partial negative charge on the sulfur atom, which then facilitates nucleophilic attack of the thiol group, in carrying out a based-catalyzed cleavage reaction.

The inventors had the insight that the high reactivity of cysteine might be explained by the presence of an amino group in the β-position to the thiol group. If the cysteine is in the zwitterion form, a carboxylate also would be in the β-position to the thiol group. Again, while not wishing to be bound by any mechanism, the inventors believe that proximity of an amino group or a carboxylate group to a thiol group enhances its reactivity in epoxide ring opening.

Accordingly, the present invention contemplates use of a thiol-containing polyphosphate that includes additional moieties that (i) enhance the reactivity of the thiol group or (ii) create a favorable environment for a thiol group to attack the epoxide. Illustrative of such additional moieties are proximate amino and carboxyl groups, or aromatic and/or a heterocyclic groups bearing a thiol group.

Accordingly, an anti-calcification agent of the present invention preferably is an amino or carboxy-thiol-containing polyphosphonate, in which an amino and/or carboxyl group facilitates the nucleophilic attack on an epoxide group in the manner envisaged for cysteine. The thiol group in such a polyphosphonate is expected to dominate the co-attachment reaction between the polyphosphonate and a polyepoxide, and to effect a more complete reaction between these two reactants, whereby the anti-calcification function of the phosphonate moiety is maximized after binding to a tissue.

In accordance with one embodiment of the present invention, such an amino or carboxy-thiol containing polyphosphonate is obtained through the chemistry of non-esterified vinylidene-polyphosphonic acid, as exemplified by Scheme 1. Thus, after an unsymmetrical aminocarboxy-containing alkyl disulfide reacts with a vinylic polyphosphonate to produce an aminocarboxy-alkyldisulfide-containing polyphosphonate, cleavage of the disulfide bond yields an aminocarboxy-thiol-containing polyphosphonate.

A preferred anti-calcification agent of the present invention is an amino-thiol-containing polyphosphonate, in which an amino group facilitates the nucleophilic attack on an epoxide group in the manner envisaged for cysteine. The thiol group in such a polyphosphonate dominates the co-attachment reaction between the polyphosphonate and a polyepoxide, and to bring these two reactants into a more complete reaction, whereby the anti-calcification function of the phosphonate moiety is maximized after binding to a tissue.

In accordance with another embodiment of the present invention, such an amino-thiol-containing polyphosphonate is obtained through the chemistry of non-esterified vinylidene-polyphosphonic acid. Thus, after an amino-containing disulfide reacts with a vinylic polyphosphonate to produce an amino-disulfide-containing polyphosphonate, cleavage of the disulfide bond yields an amino-thiol-containing polyphosphonate.

Another illustration of this type of polyphosphonate, according to the invention, is the compound 2-(2-mercaptoethylamino)-ethylidene-1,1-bisphosphonate (MABP). The synthesis of MABP, depicted in Scheme 2 below, is based on the chemistry of non-esterified vinylidene-bisphosphonic acid (VBP). In a concentrated aqueous solution, Michael addition of cystamine to VBP proceeds smoothly, to form a precursor of MABP. The latter is reduced with trimethylphosphine under mild conditions, with the cleavage of the disulfide bond and formation of the derived final product in a high yield.

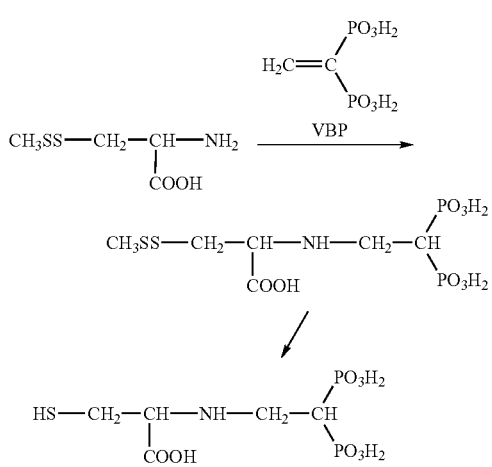

SCHEME 1

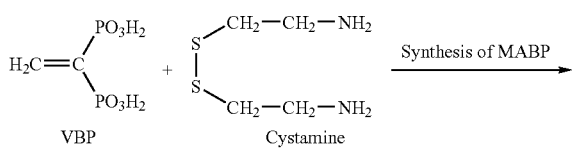

SCHEME 2
Synthesis of MABP

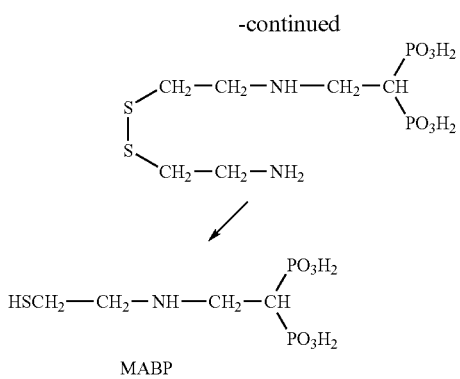

MABP

Under reaction conditions close to those of the TGA cross-linking reaction (pH 7.4; 20° C.), and at a concentration that does not interfere significantly with the cross-linking reaction (20 mM of MABP), MABP reacts with TGA-epoxy at a rate (k=1.2 1/mol*h) significantly higher than a known thiol-containing polyphosphonate, 2-mercaptoethlidene-1,1-bisphosphonate (MEBP) (k=0.035 1/mol*h), as shown in Table II. The bioprosthetic materials treated by both MABP and TGA show a significant improvement in anti-calcification ability. Consequently, it is believed that the MABP has successfully met the above-mentioned criteria, i.e., the reactive functional group is active enough to dominate the co-attachment reaction between MABP and TGA, and to cause MABP to attach to a TGA epoxide more completely.

TABLE II

Kinetics of Epoxy-ring opening with different nucleophiles (triglicidyl amine in water, 20° C., pH ca. 7)

| Substrate, concentration | Concentration of epoxide | Time of reaction | Reacted substrate | K * 10³ (1/mol * h) |
|---|---|---|---|---|
| Thiosulfate, 0.1 M | 0.3 M | 5 min | 30% | 23000 |
| | | 15 min | 52% | 17000 |
| Cysteine, 0.2 M | 0.1 M | 1 h | 13% | 1618 |
| MEBP, 0.2 M | 0.1 M | 2 h | 0.7% | 35 |
| MABP, 0.2 M | 0.06 M | 1.75 h | 10% | 1120 |

MEBP

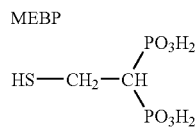

Pursuant to another embodiment of the invention, bioprosthetic materials are provided that display a prolonged resistance to calcification in vivo. Such material is obtained by subjecting bioprosthetic tissue to polyepoxide treatment in the presence of this desired amino-thiol-containing polyphosphonate, as described above. A range of tissues, conventionally employed as prosthetic components, are suitable for this treatment, according to the invention. Illustrative of these tissues are orthopedic implant where control of mineralization would be desirable, soft tissue implants whose associated mineralization would be undesirable, contact lens materials to limit mineral build up, and intra-uterine birth control devices to prevent mineralization.

EXAMPLE 1

Synthesis of MABP

Cystamine hydrochloride (3.54 g, 15.7 mmol) was dissolved in water (160 ml), passed through a column filled with a strongly basic anionite Dowex G-55 (ca. 70 ml of wet resin in OH-form), and the column was eluted with water until neutral. The resulting solution of cystamine free base (ca. 600 ml) was concentrated in vacuo to a smaller volume, acidified with VBP monohydrate (3.00 g, ca. 15 mmol) to pH 4 and further vacuum-concentrated to a thick syrup (6.14 g). VBP as a monohydrate was described previously by Alferiev et al., J. Polymer Sci., Part A (Polymer Chemistry) 39: 105 (2001). The syrup was heated at 100 to 110° C. for 7 hours, and after cooling, dissolved in water (20 ml). The solution was acidified with acetic acid (1.4 ml, 24 mmol), protected with the flow of argon, and trimethylphosphine (4.5 ml, 42 mmol) was added in one portion to the stirred mixture. During the initial 10 minutes of reaction, the temperature was not allowed to exceed 30° C. (external cooling with cold water). The self-heating then ceased, and the mixture was stirred for 3 hours at 20° to 25° C.

The reaction solution was filtered, diluted with water to 200 ml, and applied to a column with Dowex-50 (ca. 80 ml of wet resin in H-form), to remove cysteamine formed as a by-product. The column was eluted with water until neutral, and the eluate (1100 ml) was concentrated to a small volume (26 ml). Methanol (24 ml) was added to the residue gradually, and the crystallization was initiated by rubbing and/or seeding. After the end of crystallization, more methanol (17 ml) was added, and the suspension was left overnight at 4° C.

The resultant MABP crystals were filtered off, were washed portion-wise with aqueous methanol (3 volumes of methanol to 1 volume of water, 20 ml) and with methanol (ca. 70 ml), and then were dried in vacuo. Yield: 3.59 g (90%, calculated for the starting VBP). The compound was purified further by dissolving it in water (20 ml) and precipitating it with methanol (45 ml), before vacuum-drying.

NMR Structural Confirmation: ¹H NMR of MABP (D$_2$O), δ, ppm: 2.57 (tt, 21 Hz, 7 Hz, 1H, CH), 2.89 (t, 6 Hz, 2H, S—CH$_2$), 3.33 (t, 6 Hz, 2H, N—CH$_2$ of aminoethyl group), 3.50 (td, t: 14 Hz, d: 7 Hz, 2H, N—CH$_2$ of diphosphonoethyl group). ³¹P NMR of MABP (D$_2$O—water, ¹H decoupled): one peak at 16.0 ppm.

EXAMPLE 2

Crosslinking of Bioprosthetic Heart Valve Tissue with TGA in the Presence of MABP Bovine pericardium was obtained fresh at slaughter and transported to the lab on ice. After extensive rinsing with normal saline, the tissue was cut into 1 cm squares and segregated into 5 groups for crosslinking as described below. Reactions were carried out at room temperature on a rocker platform for 7 days with daily replacement of each solution with one freshly prepared in borate mannitol buffer (9.33 g/l sodium tetraborate, ~2 g mannitol to pH 7.4). Pericardial samples were removed from the reaction vessels daily, rinsed and stored individually at 4° C. in normal saline for shrink temperature determination (Ts) by Differential Scanning Colorimetric (DSC) analysis at the end of the experiment.

MABP stock solution was prepared daily by adding water, neutralizing with NaHCO$_3$, and diluting to one of the three desired concentrations (2 mM, 20 mM, 100 mM) in borate-mannitol buffer. TGA then was added to each solution to a final concentration of 100 mM TGA. Two additional groups were treated solely with 100 mM TGA in the same buffer for 7 days, and one of these treated again on day 8 with 100 mM MABP in buffer.

DSC analysis of the bioprosthetic samples showed that adequate shrink temperatures were obtained by day 6 of crosslinking, with no significant interference in the process by any condition except that of equimolar concentration of MABP and TGA. In this case, as expected, MABP quenching of the TGA-epoxy-residues grossly slowed the crosslinking process. Further experiments were done testing the anti-calcification potential of MABP co-attachment utilized the maximum non-interfering condition tested: 20 mM MABP and 100 mM TGA in borate-mannitol buffer, pH 7.4. Those experimental data are shown in Table III and graphically in FIG. 1.

TABLE III

Effect of MABP of TGA Cross-linking of Bovine Pericardium

| Day | TGA | TGA/ Day8 100 mM MABP | TGA/ 100 mM MABP | TGA/ 20 mM MABP | TGA/ 2 mM MABP |
| --- | --- | --- | --- | --- | --- |
| 1 | 72.6 +/− 1.0 | 72.2 +/− 0.8 | 67.5 +/− 0.2 | 71.1 +/− 0.6 | 73.6 +/− 1.2 |
| 2 | 77.4 +/− 0.5 | 75.7+/−0.5 | 68.1 +/− 0.3 | 74.9 +/− 0.3 | 76.8 +/− 0.3 |
| 3 | 78.2 +/− 0.3 | 76.9+/−0.2 | 69.8 +/− 1.1 | 76.5 +/− 0.5 | 77.5 +/− 1.0 |
| 4 | 79.6 +/− 0.4 | 78.7+/−0.1 | 69.2 +/− 0.5 | 79.2 +/− 0.2 | 81.0 +/− 1.2 |
| 5 | | | | | |
| 6 | 80.2 +/− 0.3 | 81.5+/−0.5 | 73.0 +/− 0.9 | 81.7 +/− 0.3 | 81.9 +/− 1.1 |
| 7 | 81.0 +/− 0.6 | | 73.9 +/− 0.5 | 82.5 +/− 0.3 | 80.9 +/ 0.3 |
| 8 | | 80.7 +/− 0.8 | | | |

EXAMPLE 3

Enhanced Calcification Inhibition Using TGA with MABP: Rat Subdermal Implant Results A series of bioprosthetic material samples were prepared, in order to compare the anti-calcification efficacy of TGA-MABP with TGA crosslinking alone. The material used were porcine aortic valve cusps, porcine aortic wall, and bovine pericardium. These materials were obtained fresh at slaughter and transported to the laboratory on ice.

All materials were rinsed thoroughly with normal saline, and 1 cm$^2$ pieces of aortic wall, pericardium, or individual cusp leaflets crosslinked with 100 mM TGA with the inclusion of 20 mM MABP, as described above with daily replacement of solutions for 7 days. After thorough rinse with normal saline, biomaterials were surgically implanted in dorsal subdermal pouches of 75–80 g male Sprague-Dawley rats as previously described. Animals were sacrificed after 21 days, implants recovered, rinsed, dried, and analyzed for Ca content by atomic absorption spectroscopy (AA).

As shown in Table IV and graphically in FIG. 2, TGA-MABP had significantly greater efficacy for inhibiting the calcification of porcine aortic wall than TGA did alone, consistently reduced the calcification of bovine pericardium as well. The inclusion of MABP had no significant effects on rat weight gain (Table IV). Thus, these data show that sulfhydryl-linking a bisphosphonate enhances the anti-calcification efficacy of TGA crosslinking.

TABLE IV

The TGA-MABP inhibition of calcification in 21-day rat subdermal implants, compared to TGA alone

| Group | Biomaterial implanted | Ca (μg/mg dry wt.) | Rat weight (g) |
| --- | --- | --- | --- |
| TGA | Aortic wall | 7.73 +/− 0.90 | 247.8 +/− 7.9 |
| TGA-MABP | Aortic wall | 0.79 +/− 0.04* | 255.0 +/− 8.6 |
| TGA | Pericardium | 11.23 +/− 4.74 | 268.2 +/− 9.9 |
| TGA-MABP | Pericardium | 1.78 +/− 0.08 | 264.4 +/− 8.4 |
| TGA(prev. exp.) | Cusp | 2.07 +/− 0.31 | — |
| TGA-MABP | Cusp | 2.06 +/− 0.12 | 269.0 +/− 3.0 |
| TGA-MABP (7 days) | Cusp | 2.24 +/− 0.05 | 268.8 +/− 6.5 |
| Glutaraldehyde | Cusp | 89.03 +/− 5.59* | 268.8 +/− 6.5 |

*p < 0.001 vs. paired TGA

What is claimed is:

1. An anti-calcification agent comprising a thiol-containing polyphosphonate comprising a thiol group and an additional reactive moiety, wherein the additional reactive moiety is at least one of an amino and a carboxy group and wherein the additional reactive moiety is in a β-position to the thiol group.

2. The anti-calcification agent of claim 1, wherein the additional reactive moiety comprises the amino group and said thiol-containing polyphosphonate is a β-amino-thiol-containing polyphosphonate.

3. The anti-calcification agent of claim 2, wherein said β-amino-thiol-containing polyphosphonate is a β-amino-thiol-containing bisphosphonate.

4. The anti-calcification agent of claim 3, wherein said β-amino-thiol-containing bisphosphonate is 2-(2-mercaptoethylamino)-ethylidene-1,1-bisphosphonate.

5. The anti-calcification agent of claim 1, wherein the additional reactive moiety comprises the carboxy group and sad thiol-containing polyphosphonate is a carboxy-thiol-containing polyphosphonate.

6. The anti-calcification agent of claim 1, wherein the additional reactive moiety comprises the amino group and the carboxy group and said thiol-containing polyphosphonate is an amino-carboxy-thiol-containing polyphosphonate.

7. A bioprosthetic article comprising a bioprosthetic tissue crosslinked with a polyepoxide and the anti-calcification agent of claim 1, wherein the anti-calcification agent is covalently bound to the polyepoxide through the thiol group.

8. A method of treating a bioprosthetic tissue, comprising contacting said bioprosthetic tissue with a polyepoxide in the presence of the anti-calcification agent of claim 1 at a temperature and for a period such that said bioprosthetic tissue crosslinks said polyepoxide and said anti-calcification agent covalently binds to said polyepoxide through the thiol group, whereby the bioprosthetic tissue displays anti-calcification properties in vivo.

9. The method of claim 8, wherein crosslinking said bioprosthetic tissue with said polyepoxide and binding of said anti-calcification agent to said polyepoxide are concurrent.

10. The method or claim 8, wherein said anti-calcification agent comprises at least one of an amino-thiol-containing polyphosphonate, a carboxy-thiol-containing polyphosphonate and an amino-carboxy-thiol-containing polyphosphonate.

11. The method of claim 10, wherein said anti-calcification agent comprises an amino-thiol-containing polyphosphonate.

12. The method according to claim 10, wherein said amino-thiol-containing polyphosphonate is produced by a process comprising (i) reacting an amino-containing disulfide with a vinylic polyphosphonate to form an amino-disulfide-containing polyphosphonate containing a disulfide bond, and (ii) cleaving the disulfide bond to form said amino-thiol-containing polyphosphonate.

13. The method according to claim 12, wherein said vinylic polyphosphonate is a vinylic bisphosphonate.

14. The method according to claim 11, wherein said amino-thiol-containing polyphosphonate is 2-(2-mercapto-ethylamino)-ethylidene-1,1-bisphosphonate (MABP).

15. The method according to claim 11, wherein a presence of said amino-thiol-containing polyphosphonate does not affect co-existing cross-linking reaction between said polyepoxide and said bioprosthetic tissue.

16. The method according to claim 8, wherein to said bioprosthetic tissue is a bioprosthetic cusp.

17. A bioprosthetic article produced by a method comprising contacting a bioprosthetic tissue with a polyepoxide in the presence of the anti-calcification agent of claim 1 at a temperature and for a period such that said bioprosthetic tissue crosslinks with said polyepoxide and said anti-calcification agent covalently binds to said polyepoxide through the thiol group, whereby said bioprosthetic article is produced and wherein said bioprosthetic article has improved anti-calcification properties in vivo.

\* \* \* \* \*

UNITED STATES PATENT AND TRADEMARK OFFICE
CERTIFICATE OF CORRECTION

| | | |
|---|---|---|
| PATENT NO. | : 7,156,881 B2 | Page 1 of 1 |
| APPLICATION NO. | : 10/336857 | |
| DATED | : January 2, 2007 | |
| INVENTOR(S) | : Robert J. Levy et al. | |

It is certified that error appears in the above-identified patent and that said Letters Patent is hereby corrected as shown below:

At column 8, line 54, delete "sad", and insert therefor --said--.

Signed and Sealed this

Tenth Day of April, 2007

JON W. DUDAS
*Director of the United States Patent and Trademark Office*